United States Patent
Joglekar

(10) Patent No.: US 10,021,012 B2
(45) Date of Patent: *Jul. 10, 2018

(54) NOTIFYING ORIGINAL STATE LISTENERS OF EVENTS IN A DOMAIN MODEL

(71) Applicant: International Business Machines Corporation, Armonk, NY (US)

(72) Inventor: Amit P. Joglekar, Olathe, KS (US)

(73) Assignee: International Business Machines Corporation, Armonk, NY (US)

(*) Notice: Subject to any disclaimer, the term of this patent is extended or adjusted under 35 U.S.C. 154(b) by 33 days.

This patent is subject to a terminal disclaimer.

(21) Appl. No.: 15/659,761

(22) Filed: Jul. 26, 2017

(65) Prior Publication Data

US 2017/0324640 A1 Nov. 9, 2017

Related U.S. Application Data

(63) Continuation of application No. 14/729,451, filed on Jun. 3, 2015.

(51) Int. Cl.
  *G06F 15/16* (2006.01)
  *H04L 12/26* (2006.01)
  (Continued)

(52) U.S. Cl.
  CPC .............. *H04L 43/12* (2013.01); *G05B 13/04* (2013.01); *G06F 11/30* (2013.01); *G06F 15/18* (2013.01);
  (Continued)

(58) Field of Classification Search
  CPC ....... H04L 43/12; H04L 43/062; H04L 43/06; H04L 43/50; H04L 41/06; H04L 41/0631;
  (Continued)

(56) References Cited

U.S. PATENT DOCUMENTS 6,335,741 B1  1/2002  Nock
6,424,354 B1  7/2002  Matheny et al.
(Continued)

FOREIGN PATENT DOCUMENTS

EP  1403763 A2  3/2004
EP  1463268 B1  6/2007
WO  0060455 A2  10/2000

OTHER PUBLICATIONS

Apache Commons, "Commons Events," The Apache Commons Dormant, Last Published Mar. 14, 2010, p. 1, The Apache Software Foundation, http://commons.apache.org/dormant/events/, Accessed on Apr. 30, 2015.

(Continued)

*Primary Examiner* — Richard G Keehn
(74) *Attorney, Agent, or Firm* — Michael O'Keefe

(57) ABSTRACT

Notifying original state listeners within a domain model. Identifying listener registration information pertaining to a listener. Monitoring a hierarchical relationship tree for an observable event, whereby the hierarchical relationship tree includes model objects, and whereby an observable event includes one or more of a change to a model object, an error condition associated with a model object, and the hierarchical relationship tree returning to an original state. Determining that a first observable event to the hierarchical relationship tree has occurred. Transmitting a notification to the listener detailing the occurrence of the first observable event. Determining that a second observable event to the hierarchical relationship tree has occurred. Determining that a third observable event to the hierarchical relationship tree has occurred, whereby the third observable event includes the hierarchical relationship tree returning to an original state. Transmitting a notification to the listener detailing the occurrence of the third observable event.

1 Claim, 7 Drawing Sheets

(51) Int. Cl.
- *H04L 12/24* (2006.01)
- *G06F 11/30* (2006.01)
- *G05B 13/04* (2006.01)
- *G06F 15/18* (2006.01)
- *G06F 19/26* (2011.01)

(52) U.S. Cl.
CPC .............. *G06F 19/26* (2013.01); *H04L 41/06* (2013.01); *H04L 41/0604* (2013.01); *H04L 41/0631* (2013.01); *H04L 43/06* (2013.01); *H04L 43/062* (2013.01); *H04L 43/50* (2013.01)

(58) Field of Classification Search
CPC ...... H04L 41/0604; G06F 11/30; G06F 15/18; G06F 19/26; G05B 13/04
See application file for complete search history.

(56) References Cited

U.S. PATENT DOCUMENTS

| | | | |
|---|---|---|---|
| 6,868,543 B1 | 3/2005 | Nusbickel | |
| 7,689,986 B2 | 3/2010 | Monnie et al. | |
| 8,401,992 B2 | 3/2013 | Hamel | |
| 9,584,394 B2 | 2/2017 | Joglekar | |
| 2001/0030664 A1* | 10/2001 | Shulman | G06Q 30/02 715/835 |
| 2004/0019669 A1 | 1/2004 | Viswanath et al. | |
| 2005/0234957 A1 | 10/2005 | Olson et al. | |
| 2007/0136743 A1* | 6/2007 | Hasek | G08B 25/085 725/33 |
| 2007/0288208 A1* | 12/2007 | Grigsby | G06Q 10/06 703/2 |
| 2009/0248828 A1* | 10/2009 | Gould | G08B 27/005 709/207 |
| 2013/0080350 A1 | 3/2013 | Bhola et al. | |
| 2016/0359714 A1 | 12/2016 | Joglekar | |

OTHER PUBLICATIONS

Ashkenas, "Backbone.js," A DocumentCloud Project, Last Updated Feb. 20, 2014, p. 1-66, Version 1.1.2, GitHub, http://backbonejs.org/, Accessed on Apr. 30, 2015.

Ho, "Notepad++ Home," Notepad++, Last Updated Apr. 16, 2015, p. 1, Version 6.7.7, http://notepad-plus-plus.org/, Accessed on Apr. 30, 2015.

Java SE, "Interface HierarchyListener," Oracle Docs—Java™ Platform Standard Ed. 7, 2014, p. 1-2, http://docs.oracle.com/javase/7/docs/api/java/awt/event/HierarchyListener.html, Accessed on Apr. 30, 2015.

Pixley, "Event Bubbling," Document Object Model Events, Nov. 13, 2000, p. 1-2, Section 1.2.3., http://www.w3.org/TR/DOM-Level-2-Events/events.html#Events-flow-bubbling, Accessed on Apr. 30, 2015.

Salam et al., "Listen to a specific attribute changes in a model in a nested collection in Backbone," Stack Overflow Questions, Apr. 27, 2013, p. 1-2, http://stackoverflow.com/questions/16250785/listen-to-a-specific-attribute-changes-in-a-model-in-a-nested-collection-in-back, Accessed on Apr. 30, 2015.

Uithol, "Backbone-relational.js," GitHub, Last Updated Oct. 25, 2014, p. 1-12, Version 0.9.0, http://backbonerelational.org/, Accessed on Apr. 30, 2015.

Joglekar, Pending U.S. Appl. No. 15/659,779, filed Jul. 26, 2017, titled: "Notifying Original State Listeners of Events in a Domain Model", pp. 1-44.

IBM: List of IBM Patents or Patent Applications Treated as Related (Appendix P), Jul. 27, 2017, pp. 1-2.

\* cited by examiner

NOTIFYING ORIGINAL STATE LISTENERS OF EVENTS IN A DOMAIN MODEL

FIELD OF INVENTION

The present invention relates generally to the field of computing, and more particularly to listener notification.

BACKGROUND

Observers, or listeners, may be employed within a piece of software to monitor events that occur within the software and take necessary actions in light of the occurring events. In order to detect desired events, listeners may be registered to an object, or subject, through an application programming interface in order to monitor changes in object features. Listeners may implement an interface prescribed by the object in order to receive notifications about the occurrence of certain events.

Domain modeling describes a means for understanding real world entities and the relationships between those entities. Domain modeling may provide various approaches related to solving a specific problem. A domain model may include a network of model objects that represent various entities within the domain model. A model object may define certain application programming interfaces for registering and unregistering listeners.

SUMMARY

Embodiments of the present invention disclose a system, method, and program product for notifying original state listeners within a domain model. A computer identifies listener registration information pertaining to a listener, whereby the listener registration information includes information detailing one or more model objects corresponding to the listener and information detailing a listener type of the listener, and whereby the listener receives one or more notifications, and whereby the one or more notifications are received only when at least one of an initial change occurs to one or more model objects in a hierarchical relationship tree, an initial error condition occurs to one or more model objects in a hierarchical relationship tree, and a change to one or more model objects that returns the hierarchical relationship tree to an original state. The computer monitors a hierarchical relationship tree for an observable event, whereby the hierarchical relationship tree includes one or more model objects, and whereby an observable event includes one or more of a change to at least one of the one or more model objects in the hierarchical relationship tree, an error condition associated with at least one of the one or more model objects in the hierarchical relationship tree, and the hierarchical relationship tree returning to an original state. The computer determines that a first observable event to the hierarchical relationship tree has occurred. The computer transmits a notification to the listener detailing the occurrence of the first observable event. The computer determines that a second observable event to the hierarchical relationship tree has occurred. The computer determines that a third observable event to the hierarchical relationship tree has occurred, whereby the third observable event includes the hierarchical relationship tree returning to an original state. The computer transmits a notification to the listener detailing the occurrence of the third observable event.

DETAILED DESCRIPTION

Figure 1:
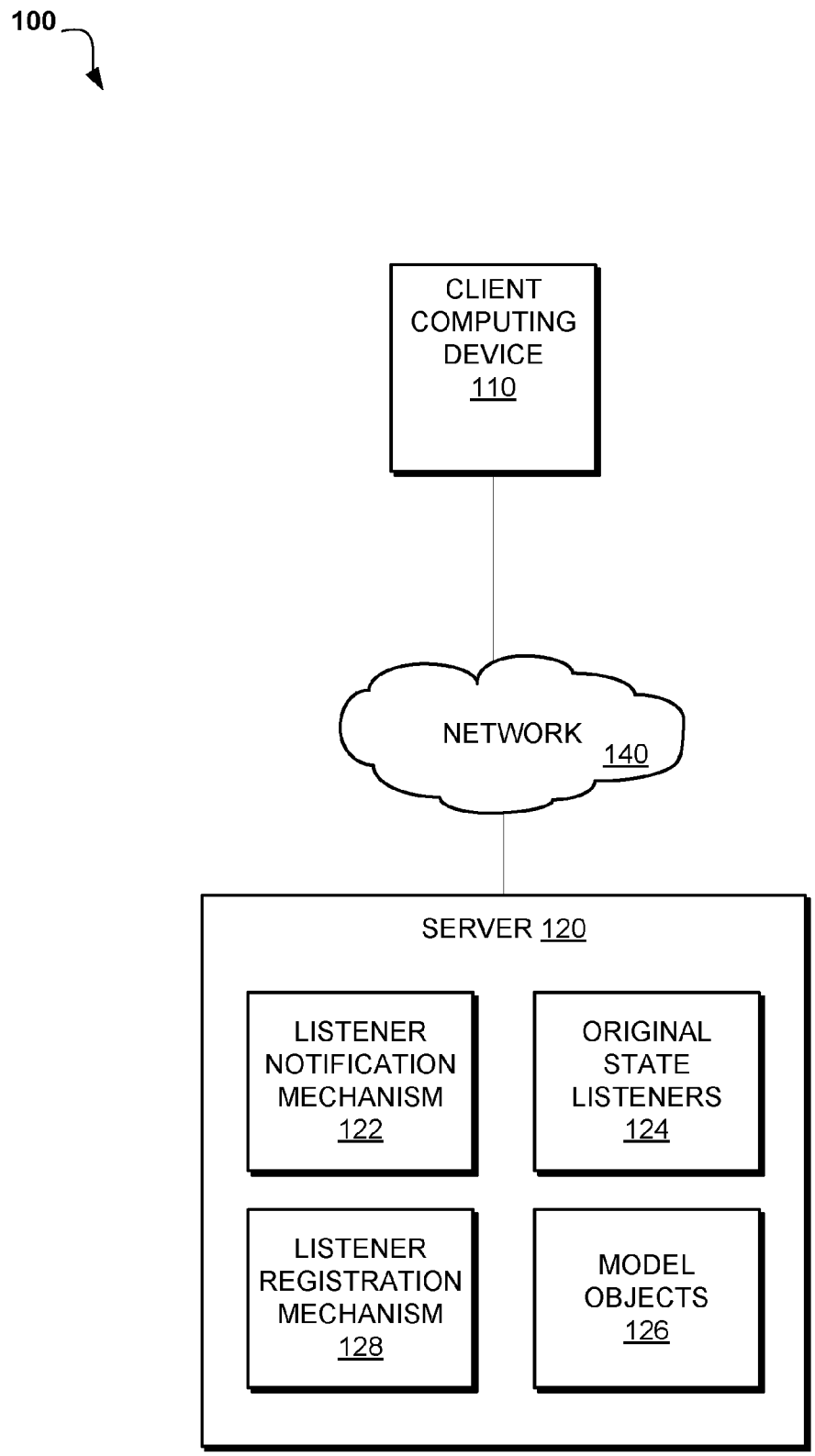
FIG. 1 is an illustration of an exemplary architecture for a listener notification system, in accordance with one embodiment of the present invention.

Embodiments of the present invention are directed to notifying listeners of observable events only upon changes that alter the original state of a model object or hierarchical relationship tree in a complex domain model and changes that return the model object or hierarchical relationship tree to the original state.

Listeners registered to a model object within a domain model may be notified when a change is made to a feature within the model object. A feature may refer to a model object attribute or a model object reference. An attribute may be a property of the model object, which includes the name and type of the attribute. For example, for a "Book" model object, "numPages" may be the name of an attribute that relates to the number of pages in a book. The attribute type may also be defined as "integer", which may indicate the acceptable data entry values for the attribute are numerical values.

A reference may represent an association between two model objects, which may include a reference name and a reference type. The reference type of a model object may represent the model object to which the subject model object is associated. For example, if a "Book" model object has a reference to an "Author" model object, then the "bookAuth" reference name is of the type "Author." In turn, the "Author" model object may also have attributes of its own of type string, such as "firstName" relating to the first name of the author, "lastName" relating to the last name of the author, and "address" relating to the address of the author. References among various model object in a domain model may create a network of model objects linked to each other by references. The resulting network of model objects may have a hierarchical tree structure. For example, a "Library" model object may have a reference to "Section" model objects, which may be used for classifying items based on genre types, such as fiction, science, or history. The "Section" model objects may in turn have additional references to "Book" or "DVD" model objects. Therefore, each model object references to other model objects in a tree-like structure.

Each feature may be categorized as either singular or multiplicity-many. A singular reference has only one object in the association. For example, a "Library" model object may have a singular reference to a "Librarian"-type model object since a library may only have one librarian. A multiplicity-many reference may be a reference with more than one object in an association. For example, an "Author" model object may have a multiplicity-many reference with more than one "Book"-type model object if the author has written more than one book.

A listener registration mechanism may be a mechanism, or tool, that registers listeners to specific model objects within a domain model. Depending on provisions made by the listener registration mechanism, a listener may be registered to receive notification about changes to a specific feature in a model object. Additionally, if a specific feature is not specified, the listener may be registered to receive notifications when any of feature associated with the model object is changed. When a notification is sent to a listener upon a feature change within the model object, the notification may include details, such as the model object, the feature that was changed, the type of change to the feature, the previous value of the feature, and current value of the feature.

A listener may be classified as a direct listener or an indirect listener. A direct listener may be a listener registered to receive notifications whenever a change is made to an attribute in a model object to which the listener is registered. For example, if a domain model includes three model objects, such as model object A, model object B, and model object C, where model object A is an "Author" model object and model object B and model object C are "Book" model objects each connected as a multiplicity-many reference from model object A, a direct listener may be registered to model object A. Whenever a change is made to model object A, such as when the address of an author is changed, the direct listener is notified of the change within model object A.

An indirect listener may be a listener registered to a model object in a hierarchical relationship tree, or tree, of model objects within the domain model where the indirect listener may receive notifications of changes to any model object lower in the hierarchical relationship tree than the model object to which the indirect listener is registered. For example, with respect to the domain model in the preceding example, an indirect listener may be registered to model object A to receive notifications whenever a change is made to model object B or model object C, since model object B and model object C are below model object A in the hierarchical relationship tree. Furthermore, if model object B is connected as a reference to model object D and model object E, the indirect listener registered to model object A would receive notification whenever a change is made to model object D or model object E since both of those model objects are within the hierarchical relationship tree of model object A. A hierarchical tree may relate to the model objects cascading down from a listener registered model object. The hierarchical tree may include a subnetwork of model objects within the domain model. For example, if a listener is registered to model object A and model object A is connected as a reference to model object B and model object C, then model object B and model object C are a part of the hierarchical relationship tree for model object A. As previously described, references among various model objects in a domain model may create a hierarchical relationship tree through associations with other model objects in the domain model. Therefore, if the listener registration mechanism allows granularity of specifying the model object feature for which a listener would like to register, the listener registration mechanism may allow indirect listeners to specify a reference, rather than an attribute, to which the indirect listener may register. Similarly, the listener registration mechanism may allow direct listeners to specify an attribute, rather than a reference, to which the direct listener may register.

Typically, listeners registered to model objects receive notifications of feature changes within the model object. A model object change may be any feature change to the model object from the initial state of the model object when the domain model was opened or previously saved by a user. However, a listener may also wish to receive notifications upon the occurrence of an observable event. An observable event may be any event involving the model object in which a listener may be interested. Although an observable event may include a feature change to a model object, an observable event may also include the presence of an error condition in the model object as a result of a change to the model object. The error condition may be a warning or message that conveys information to the user that made the change. For example, an error condition may include entered data not conforming to the model object properties, such as a required name not being specified or a negative value being assigned to an attribute only supporting positive values.

A listener notification mechanism may be a tool capable of issuing notifications to registered listeners whenever an observable event occurs within a model object or hierarchical relationship tree. When registering to receive observable event notifications from a listener notification mechanism, a listener may expect to limit the reception of notifications based on an initiation criteria and a completion criteria. For example, an indirect listener may wish to receive a single change notification upon the first change anywhere within the hierarchical relationship tree of model objects cascading down from the listener registered model object. The listener may not wish to receive notifications of subsequent changes to model objects within the tree until a change event occurs that matches the completion criteria. For example, the listener in the previous example may expect to receive only one more notification when the last change within the tree is removed or reverted back to its original state.

Many typical change notification mechanisms may only be able to send notifications each time a change within the tree is made. For example, if a domain model includes three model objects, such as model object A, model object B, and model object C, model object A may be atop a tree and model object B and model object C may be connected as references from model object A. Furthermore, model object B and model object C are displayed in a tabular format where the first row of the table corresponds to model object A and the second row of the table corresponds to model object B. Additionally, columns in the table may display specific attributes of each row-specific model object. If model object A is of type "Author" and model object B and model object C are of type "Book", then the first row of the table may display attributes of the first book, such as name, genre, number of pages, and price. Similarly, the second row of the table may display attributes of the second book. Furthermore, a change indicator icon may be shown beside the table to indicate when a change has been made to a book.

If an indirect listener is registered to model object A to receive notifications of changes to model object B and model object C and a change occurs in model object B, a notification would be sent to the indirect listener registered to model object A and the indirect listener would take an appropriate action, such as displaying a change indicator beside the table user interface in the graphical user interface to indicate a change was made by a user. If a second change occurred in the tree to model object C, another notification would be sent to the indirect listener registered to model object A since another change has occurred within the tree to which the indirect listener is registered. However, since the change indicator is already displayed beside the table user interface, the indirect listener may not wish to receive a second notification about this change. Thereafter, the first change made to model object B is removed and model object B is returned to its original state. Since the change to model object C still exists, the change indicator beside the table user interface cannot be removed. Therefore, the indirect listener does not wish to receive a change removed notification after model object B is returned to its initial state. Finally, model object C is returned to the original state. The indirect listener would now expect to receive a change removed notification and remove the change indicator beside the table user interface, since there are no longer any changes to objects within the tree to which the listener is registered. As such, it may be advantageous, among other things, to implement a change notification mechanism that allows listener registration of an indirect listener to receive a single notification upon the first occurrence of an observable event within a hierarchical relationship tree and upon removal of the last observable event within the same hierarchical relationship tree. Similarly, a change notification mechanism may allow listener registration of a direct listener to receive a single notification upon the first occurrence of an observable event within an object and upon removal of the last observable event within the same object. When notification is sent to such a listener, the notification may additionally include information identifying whether the event is the first observable event to the object or tree or an event that returns the object or tree to an original state.

According to one embodiment, a listener notification mechanism may support a listener that wishes to only receive a notification upon the initial observable event to a model object or a hierarchical relationship tree and another notification upon the removal of the last observable event, or the terminal observable event, from the same model object or the same hierarchical relationship tree. Such a listener may be referred to as an original state listener, since the listener only wishes to receive a single occurrence notification upon the happening of a first observable event resulting in a change from the original state and a single removal notification when a last observable event is removed resulting in return back to the original state without notification of any intervening observable events. An original state listener may include subclass types of listeners, such as direct original state listeners and indirect original state listeners. Therefore, embodiments of the present invention may have the capacity to improve the technical field of listener notification by conserving system resources and preventing system errors encountered by sending unnecessary notifications to listeners during the modification of model object features within a hierarchical relationship tree.

FIG. 1 is an illustration of an exemplary architecture of a listener notification system, in accordance with one embodiment of the present invention. The listener notification system 100 may include a server 120 and client computing device 110, all interconnected over a network 140. Generally, the networked computer environment 100 may include a plurality of client computing devices 110 and servers 120, in accordance with embodiments of the invention.

The communication network 140 may include various types of communication networks, such as a wide area network (WAN), local area network (LAN), a telecommunication network, a wireless network, a public switched network and/or a satellite network, and may include connections, such as wire, wireless communication links, or fiber optic cables. In general, communication network 140 can be any combination of connections and protocols that will support communications between client computing device 110 and server 120, in accordance with embodiments of the invention.

In various embodiments of the invention, a client computing device 110 may be, for example, a laptop computer, tablet computer, netbook computer, personal computer (PC), a desktop computer, a personal digital assistant (PDA), a smart phone, or any type of computing device capable of running a program, and accessing a network.

Server computer 120 may be a laptop computer, netbook computer, personal computer (PC), a desktop computer, or any programmable electronic device capable of hosting a listener notification mechanism 122, original state listeners 124, model objects 126, listener registration mechanism 128, and communicating with client device 110 via network 140, in accordance with embodiments of the invention. Server computer 120 may include internal and external hardware components, as depicted and described in further detail below with reference to FIG. 7. Server 120 may also operate in a cloud computing service model, such as Software as a Service (SaaS), Platform as a Service (PaaS), or Infrastructure as a Service (IaaS). Server 120 may also be located in a cloud computing deployment model, such as a private cloud, community cloud, public cloud, or hybrid cloud.

In accordance with one embodiment and as previously described, original state listeners 124 may await changes in a piece of software and take necessary actions in light of the occurring events. As previously described, original state listeners 124 may be listeners registered to receive notifications of changes within model objects to which direct original state listeners are registered or for changes within the hierarchical relationship trees cascading down from the model objects to which the indirect original state listeners are registered. However, original state listeners 124 may only receive notification of an observable event upon occurrence of the initial observable event within the object or the hierarchical relationship tree and upon an observable event that returns the object or hierarchical relationship tree to its original state. For example, if an indirect original state listener among original state listeners 124 is registered to model object A that has a reference with model object B and a separate reference to model object C within its hierarchical relationship tree and the first occurrence of an observable event within the hierarchical relationship tree is a change to model object B, then the original state listener would be notified. If subsequent observable events occurs within the hierarchical relationship tree, the original state listener would not be notified again unless all previous observable events, including the change within model object B, are removed, which would return the hierarchical relationship tree for model object A to its original state, or the user completes implementation dependent actions that save and sync the domain model with a reference point. For example, if a domain model for a database is used to generate SQL commands for changes made to the database, the change indicators in the domain model user interface may be removed when the user has executed SQL commands to bring the domain model in sync with the database. Original state listeners 124 may be registered to a model object 126, through an application programming interface in order to receive notifications of changes in model object features. The actual listener registration may be handled by listener registration mechanism 128.

Model objects 126 are elements within a domain model. Each model object within model objects 126 within the domain model has associated features, such as attributes and references. A model object attribute is a property of the model object, such as the name and type of the attribute. A model object reference is an association between two model objects within the domain model, such as a reference name and a reference type.

Listener registration mechanism 128 may be a tool that registers listeners, including original state listeners 124, to model objects 126 based on user preferences to allow notifications of observable events within the model objects 126 to be sent to the registered listeners. The task of sending notifications of observable events may be carried out by listener notification mechanism 122. When registering a listener, listener registration mechanism 128 may require particular listener registration information, such as the corresponding model object and feature to which the listener is registering and the corresponding listener type. The listener registration mechanism 128 may support the registration of various listener types, including direct listeners, indirect listeners, and original state listeners 124, such as direct original state listeners and indirect original state listeners. When a listener registers with the listener registration mechanism 128 to receive notifications of observable events to a model object within model objects 126, the listener may specify registration details, such as the model object within model objects 126 to which the listener is registering, particular features within the model object to which the listener is registering, and whether the listener is registering as a direct listener, an indirect listener, or an original state listener within original state listeners 124. Listener registration mechanism 128 may maintain separate lists of each type of listener registered to the domain model to allow more efficient notification of observable events.

As previously described, depending on the granularity allowed by listener registration mechanism 128 and listener notification mechanism 122, a direct listener and direct original state listener from original state listeners 124 may be registered to receive a notification about an observable event in a specific attribute of the model object to which the direct listener is registered. Similarly, an indirect listener and indirect original state listener from original state listeners 124 may be registered to receive a notification about an observable event inside the hierarchical relationship tree cascading down from a specific reference in the model object to which the indirect listener is registered.

Listener notification mechanism 122 may be a tool that sends notifications of observable events, for which the listeners are registered, to registered listeners. Listener notification mechanism 122 may be capable of notifying various types of listeners, including direct listeners, indirect listeners, and original state listeners 124. Listener notification mechanism 122 may monitor the domain model for observable events and send notifications to registered listeners based on a notification algorithm that determines which registered listeners may receive notifications. The notification algorithm may take into account various domain model structural factors and a variety of model object changes, such as the hierarchical relationship tree structure of the domain model, whether the feature change is an attribute change or a reference change, whether a changed feature is a multiplicity many feature, whether an observable event has already occurred within a hierarchical relationship tree, whether the model object associated with a newly added reference already has an observable event in the corresponding hierarchical relationship tree to that model object, and whether the model object associated with a removed reference had an observable event in the corresponding hierarchical relationship tree to that model object. Using the various domain model structural factors and the variety of model object changes, the listener notification mechanism 122 may understand details of the domain model structure, such as model object hierarchy, and the status of any observable events within the domain model.

Figure 2:
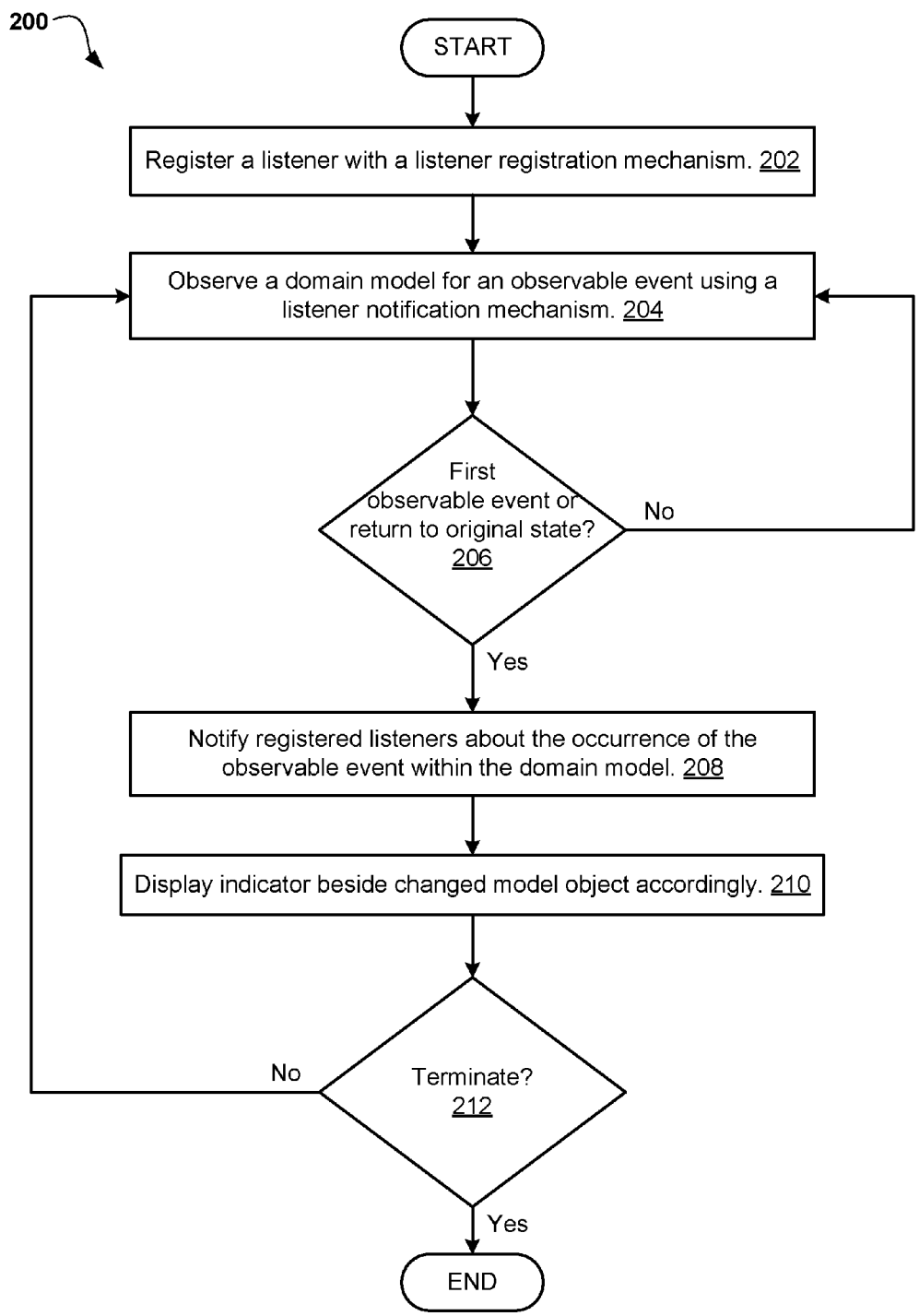
FIG. 2 is a flowchart depicting the operational steps of the listener notification system of FIG. 1, in accordance with one embodiment of the present invention.

Referring now to FIG. 2, a flowchart 200 of the operational steps carried out by the listener notification system 100 of FIG. 1 are depicted, in accordance with one embodiment of the present invention. In the example embodiment, a listener deployed to a domain model may be registered to a model object within model objects 126 (step 202). When registering with the listener registration mechanism 128, a listener may specify the model object 126 to which the listener may wish to register, the model object feature for which the listener wishes to monitor, and a listener type, such as direct, indirect, and original state, corresponding to the listener. Since each type of listener may receive notifications under different circumstances, the listener registration mechanism 128 may maintain a separate list for each type of listener that registers to model objects 126 within the domain model, such as a list of direct listeners, a list of indirect listeners, a list of indirect original state listeners, and a list of direct original state listeners. For example, the listener registration mechanism 128 may group all direct original state listeners for the model object in a single list since the direct original state listeners of a domain model may wish to receive notifications under similar circumstances. Additionally, before adding a listener to a list, the listener registration mechanism 128 may perform a check to determine whether the observable event the listener is attempting to register for corresponds to a feature supported by that type of listener. Direct listeners may only register for notifications of attribute changes to model objects 126 and indirect listeners may only register for reference changes to model objects 126. If a listener is attempting to register for a feature not supported by that type of listener, the listener registration mechanism 128 may send an error message to the user regarding the failed listener registration.

Once the listener registration mechanism 128 registers a listener, the listener notification mechanism 122 may then begin to monitor the model objects 126 contained within the domain model for observable events (step 204). As previously described, an observable event may be any event to the model object for which the listener may be registered, such as changes and error conditions.

Listener notification mechanism 122 then determines whether a first observable event has occurred or whether an observable event that returns a model object or its hierarchical relationship tree to its original state has occurred (step 206). Depending on granularity allowed by listener registration mechanism 128 and listener notification mechanism 122, an observable event may be within an object or attribute to which a direct original state listener is registered or a hierarchical relationship tree of an object or reference to which an indirect original state listener is registered.

When an observable event occurs, if listener notification mechanism 122 determines that the observable event is not a first observable event within an object or attribute or the observable event does not return the hierarchical relationship tree of an object or reference to its original state (step 206, "NO branch"), then the listener notification mechanism 122 continues to observe the domain model for observable events (step 204).

When an observable event occurs, if listener notification mechanism 122 determines the observable event is a first observable event within an object or attribute or the observable event returns the hierarchical relationship tree of an object or reference to its original state (step 206, "YES branch"), then listener notification mechanism 122 proceeds to notify the original state listeners 124 registered to receive notifications of the observable event (step 208). The notification algorithm may be utilized by listener notification mechanism 122 to analyze the observable event to determine whether the observable event is a first observable event within an object or a hierarchical relationship tree or returns the object or hierarchical relationship tree to its original state by determining whether other observable events exist within the object or hierarchical relationship tree. The notification algorithm may assist listener notification mechanism 122 in determining when to send notifications to the appropriate registered original state listeners 124 based on existing conditions within the domain model. As previously described, the notification algorithm may be an algorithm programmed to take into account various domain model structural factors and a variety of existing model object changes in order to notify the appropriate registered listeners.

Since an original state listener within original state listeners 124 is registered to only receive notifications upon the occurrence of the first observable event and an observable event that returns the object or hierarchical relationship tree to its original state, listener notification mechanism 122, applying the notification algorithm, may need to determine the presence of existing observable events within the changed model object as well as other model objects both above and below the changed model object in the hierarchical relationship tree. For example, a hierarchical relationship tree may contain a model object A in a top tier of the hierarchical relationship tree with a model object B and a model object C in a bottom tier. A reference may exist between model object A and model object B and also between model object A and model object C. As previously described, a reference may represent an association between two model objects. If an indirect original state listener is registered to model object A and a first observable event occurs within the hierarchical relationship tree that affects model object B, a notification will be sent to the original state listener registered to model object A. If subsequent observable events occur within the hierarchical relationship tree, the original state listener would not be notified again unless all the previous observable events, including the change within model object B, are removed, which would return the hierarchical relationship tree for model object A to its original state.

When sending notifications to registered listeners, listener notification mechanism 122 may send notifications to the various listeners in a hierarchy depending on the type of listener. If changed feature is an attribute, the listener notification mechanism 122 may first send notifications to direct listeners on the list of direct listeners registered to the model object within model objects 126 in which the observable event occurred. If changed feature is a reference, listener registration mechanism 122 may then send notification of the observable event to indirect listeners for the reference change in the list of indirect listeners. The listener registration mechanism 122 may then send notification to any original state listeners 124, such as direct original state listeners and indirect original state listeners, for the feature change in the list of original state listeners. Since the listener registration mechanism may only send notification of the observable event to original state listeners if the observable event is either the first to occur within the object or hierarchical relationship tree or returns the object or hierarchical relationship tree to an initial state, the listener notification mechanism 122 may implement the notification algorithm to determine if notifying the original state listeners is warranted for an observable event.

Upon detecting a first observable event or an observable event that returns an object or a hierarchical relationship tree to an original state, a listener within original state listeners 124 may also display a change indicator, such as a blue triangle, accordingly (step 210). A change indicator may be displayed beside the user interface display for a changed model object within model objects 126 to indicate data in that model object or its hierarchical relationship tree may have changed. Conversely, a displayed change indicator may remain beside the changed model object until either a user saves the domain model or an observable event occurs that returns the model object or hierarchical relationship tree to its original state. Additionally, the listener may display an error condition indicator, such as a red "X", beside a model object which is not in conformity with acceptable parameters. For example, a feature may be within error condition parameters if a text string was entered into a field where only integers are acceptable entries. The error condition indicator may remain displayed until the feature is returned to the original state or the feature is changed to conform to acceptable feature parameters. Furthermore, the change indicator and error condition indicator may be displayed adjacent to the user interface corresponding to each model object higher up in the hierarchical relationship tree than the changed model object. For example, if a hierarchical relationship tree has three tiers, Tier 1, Tier 2, and Tier 3, and a change occurred to a model object in Tier 2, then a change indicator is displayed adjacent to the changed model object within Tier 2 of the hierarchical relationship tree as well as beside the model objects in Tier 1 that are above the changed model object. However, the change indicator is not displayed in model objects in Tier 3 below the changed model object.

Next at step 212, it may be determined whether the method may terminate. According to one implementation, the method may terminate based on various circumstances, such as a user shutdown of the system hosting listener registration mechanism 128 and listener notification mechanism 122. If it is determined that the method should terminate, then the method may end. However, if at 212, it is determined that the method should not terminate, then the method may continue back to step 204 to monitor the domain model for an observable event.

Figure 3:
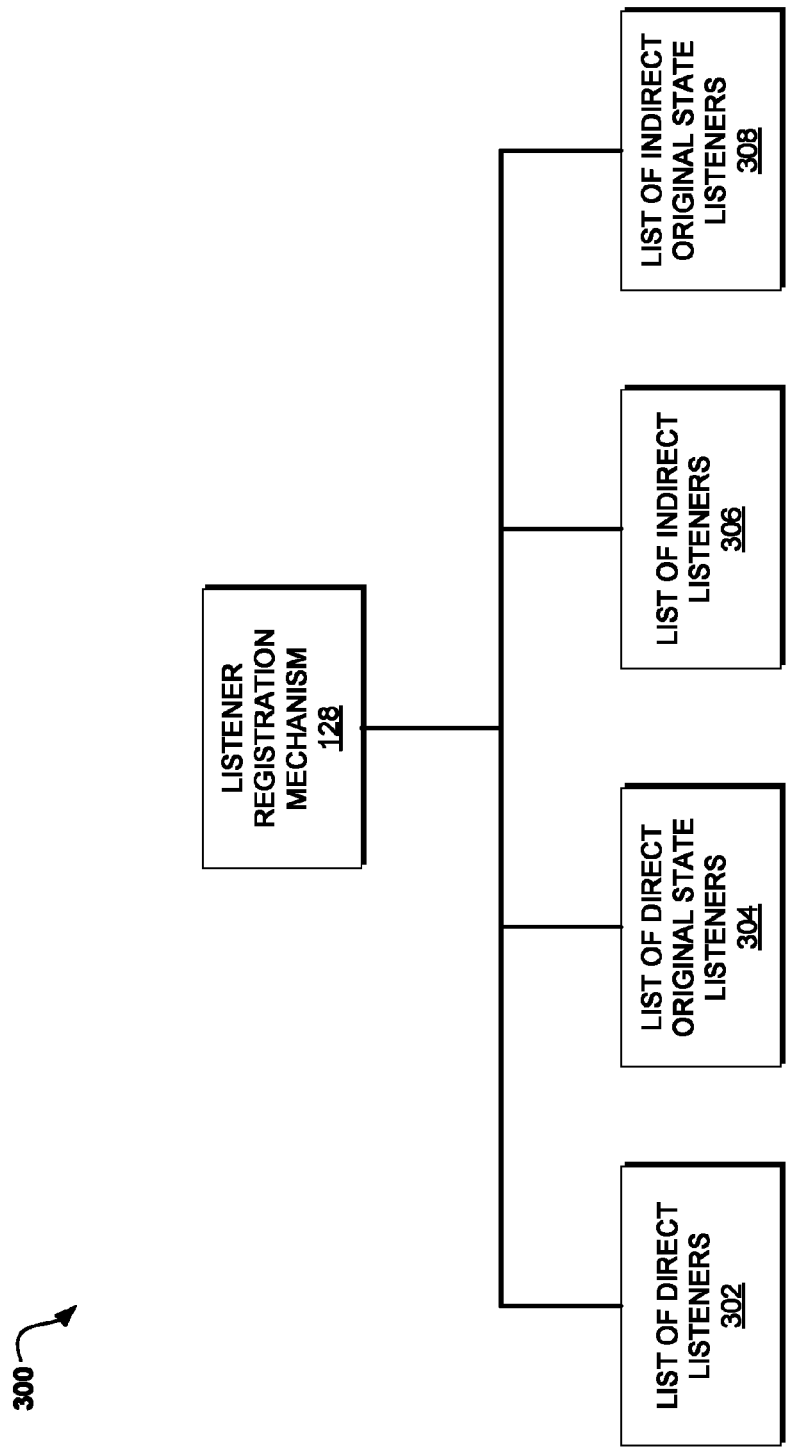
FIG. 3 is a functional block diagram of the listener registration mechanism of FIG. 1, in accordance with an embodiment of the present invention.

Referring now to FIG. 3, a functional block diagram 300 of the listener registration mechanism 128 of FIG. 1 is depicted, in accordance with one embodiment of the present invention. The listener registration mechanism 128 may maintain lists for each type of listener, including a list of direct listeners 302, a list of direct original state listeners 304, a list of indirect listeners 306, and a list of indirect original state listeners 308. Since each type of listener may receive notifications under different circumstances, an independent list for each type of listener may be maintained by the listener registration mechanism 128. Before adding a listener to a list, the listener registration mechanism 128 may perform a check to determine whether the observable event the listener is attempting to register for is permissible for that type of listener. For example, if listener registration mechanism 128 supports specification of a feature of model objects 126 which a listener wants to monitor, direct original state listeners may register for notifications of attribute changes to a model object but indirect original state listeners 124 may only register for references to get notifications of changes to the hierarchical relationship tree cascading down from a reference. If a listener is attempting to register for a feature that is not supported by that type of listener, the listener registration mechanism 128 may send an error message to the user regarding the failed listener registration.

Figure 4:
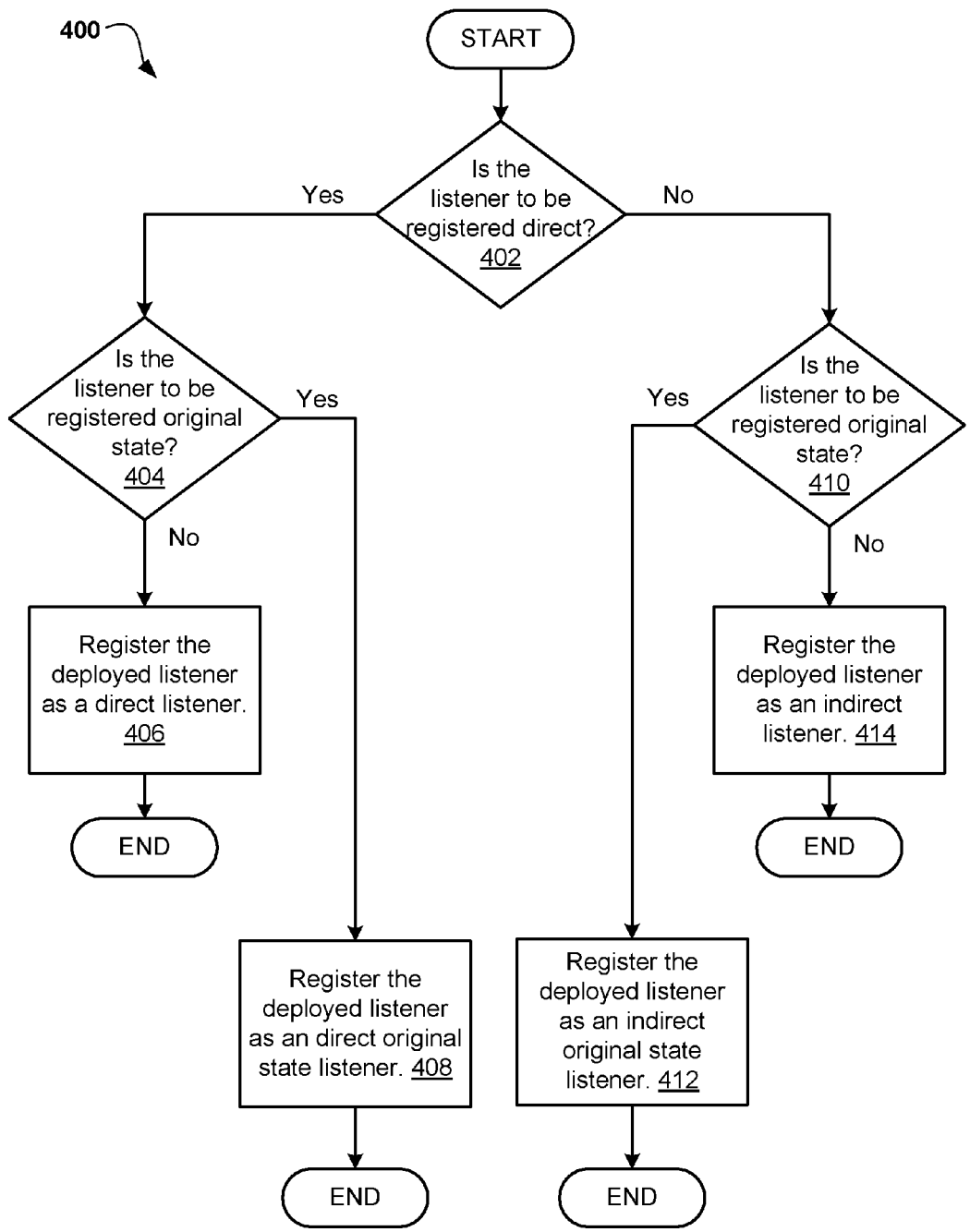
FIG. 4 is a flowchart depicting the operational steps of the listener registration mechanism of FIG. 1, in accordance with one embodiment of the present invention.

Referring now to FIG. 4, an operational flowchart 400 illustrating the steps taken by a listener registration mechanism 128 while registering listeners is depicted, in accordance with one embodiment of the present invention. When registering listeners, the listener registration mechanism 128 may first determine whether the listener being registered is a direct listener or an indirect listener (step 402). If the listener registration mechanism 128, based on user preferences, determines the listener is a direct listener, then the listener registration mechanism 128 may then determine whether the direct listener is being registered as a direct original state listener within original state listeners 124 (step 404). If listener registration mechanism 128 determines, based on user preferences, a direct listener is not registering as a direct original state listener registration mechanism 128 will add the listener to the list of direct listeners 302 (step 406). If, in step 404, the listener registration mechanism 128, determines, based on user preferences, the listener is a direct original state listener, listener registration mechanism 128 will add the listener to the list of direct original state listeners 304 (step 408). If, in step 402, listener registration mechanism 128 determines a listener is an indirect listener, the listener registration mechanism 128 may determine whether the listener is an indirect original state listener from original state listeners 124 (step 410). If the listener registration mechanism 128 determines, based on user preferences, the listener is an indirect original state listener, then listener registration mechanism 128 may register the listener as an indirect original state listener and add the listener to the list of indirect original state listeners 308 (step 412). If, in step 410, the listener registration mechanism 128, based on user preferences, determines the listener is an indirect listener, then the listener registration mechanism 128 may register the listener as an indirect listener and add the listener to the list of indirect listeners 306 (step 414).

Figure 5:
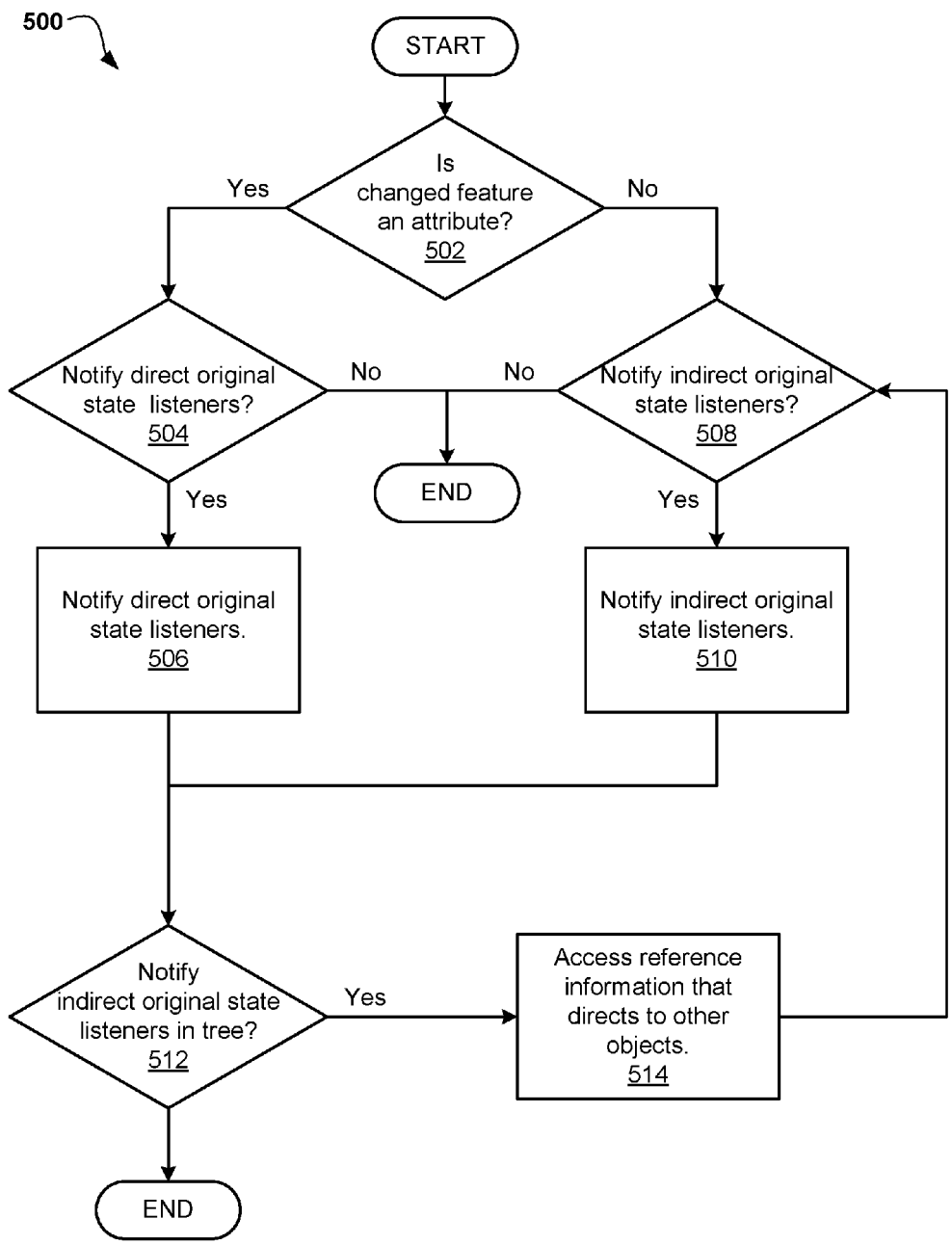
FIG. 5 is a flowchart depicting the operational steps of the listener notification mechanism of FIG. 1 when notifying registered listeners of observable events, in accordance with one embodiment of the present invention.

Referring now to FIG. 5, a functional block diagram of the listener notification mechanism 122 notifying registered original state listeners 124 of an observable event is depicted, in accordance with one embodiment of the present invention. When sending notifications to registered original state listeners, the listener notification mechanism 122 may send notifications to the various listeners in a hierarchy depending on the type of listener and the particular level of the hierarchical relationship tree the model object or reference in which the observable event occurs is located. The listener notification mechanism 122 may first determine whether an observable event affects an attribute or a reference (step 502). If the observable event affects an attribute (step 502, "YES" branch), listener notification mechanism 122 may then determine whether to notify direct original state listeners, at the current level of the hierarchical relationship tree, registered to the model object in which the attribute was changed (step 504). If the observable event does not affect an attribute (step 502, "NO" branch), then the observable event may affect a reference and listener registration mechanism may then determine whether to notify indirect original state listeners at the current level of the hierarchical relationship tree registered to the model object in which the reference was changed (step 508).

If the observable event affects an attribute (step 502, "YES" branch), listener notification mechanism 122 may then determine whether to notify direct original state listeners at the current level of the hierarchical relationship tree registered to the model object in which the attribute was changed (step 504). If listener notification mechanism 122 determines direct original state listeners at the current level of the hierarchical relationship tree registered to the model object should be notified (step 504, "YES" branch), then listener notification mechanism 122 may notify the applicable direct original state listeners at the current level of the hierarchical relationship tree (step 506). Once listener notification mechanism 122 notifies the applicable direct original state listeners at the current level of the hierarchical relationship tree (step 506), listener notification mechanism 122 may then determine whether to notify any indirect original state listeners higher up in the hierarchical relationship tree (step 512). If, at step 504, listener notification mechanism 122 determines direct original state listeners at the current level of the hierarchical relationship tree should not be notified (step 504, "NO" branch), then the method may terminate.

If the observable event does not affect an attribute (step 502, "NO" branch), then the observable event may affect a reference and listener registration mechanism may then determine whether to notify indirect original state listeners at the current level of the hierarchical relationship tree registered to the model object in which the reference was changed (step 508). If listener notification mechanism 122 determines indirect original state listeners at the current level of the hierarchical relationship tree should be notified (step 508, "YES" branch), then listener notification mechanism 122 may notify the applicable indirect original state listeners at the current level of the hierarchical relationship tree (step 510). Once listener registration mechanism has notified all indirect original state listeners at the current level of the hierarchical relationship tree (step 510), listener notification mechanism 122 may then determine whether to notify any indirect original state listeners higher up in the hierarchical relationship tree (step 512). If, at step 508, listener notification mechanism 122 determines indirect original state listeners at the current level of the hierarchical relationship tree should not be notified ("NO" branch), then the method may terminate.

If listener notification mechanism 122 determines indirect original state listeners higher up in the hierarchical relationship tree should be notified (step 512, "YES" branch), listener notification mechanism 122 may access reference information that directs listener notification mechanism 122 to the indirect original state listeners higher up in the hierarchical relationship tree (step 514). Once listener notification mechanism 122 has obtained the reference information needed to identify the indirect original state listeners higher up in the hierarchical relationship tree, listener registration mechanism 122 may return to step 508 to determine whether the indirect original state listeners at this new current level of the hierarchical relationship tree should be notified. If listener notification mechanism 122 determines indirect original state listeners higher up in the hierarchical notification tree should not be notified (step 512, "NO" branch), then the method may terminate.

Figure 6:
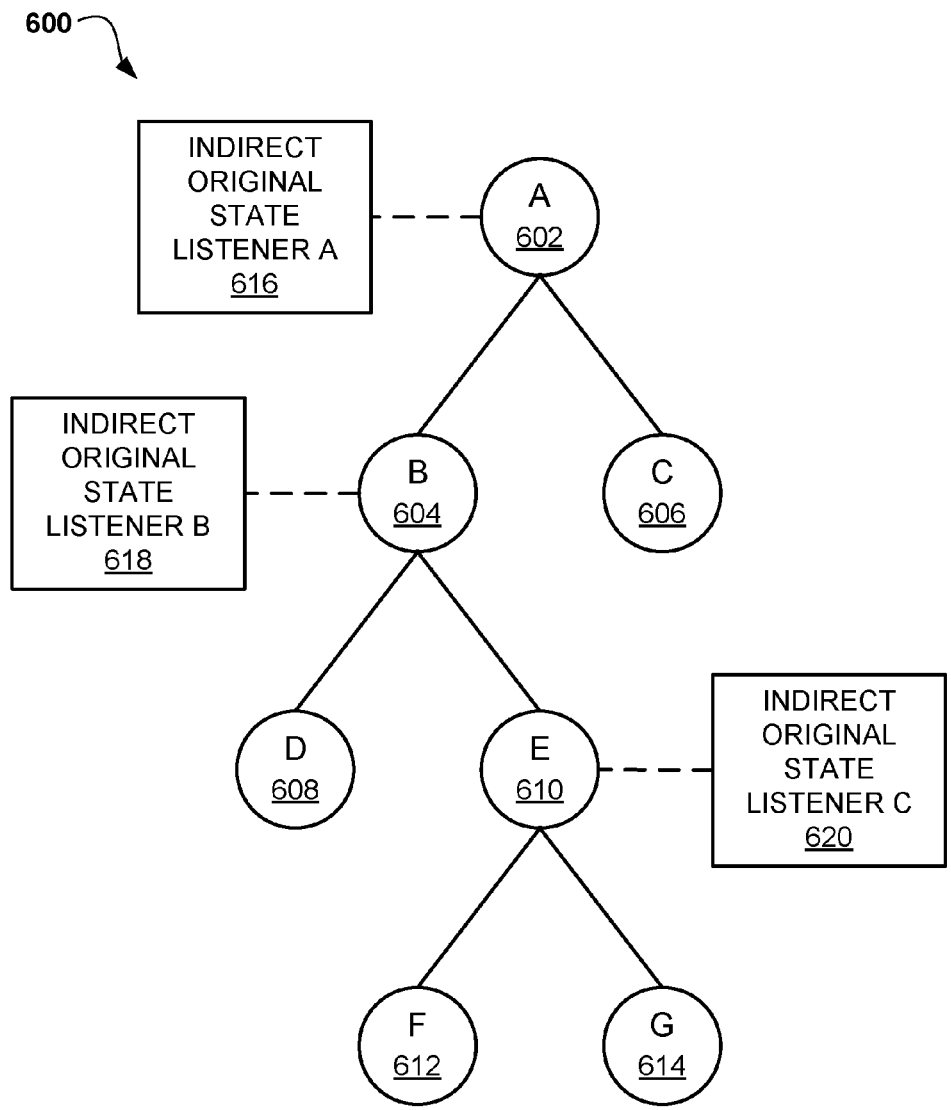
FIG. 6 is a functional block diagram of a hierarchical relationship tree with registered indirect original state listeners, in accordance with one embodiment of the present invention.

FIG. 6 depicts a functional block diagram 600 of a hierarchical relationship tree with registered indirect original state listeners, in accordance with one embodiment of the present invention. A hierarchical relationship tree may contain model object A 602, model object B 604, model object C 606, model object D 608, model object E 610, model object F 612, and model object G 614. Additionally, three indirect original state listeners may be registered to model objects within the hierarchical relationship tree. Indirect original state listener A 616 may be registered to model object A 602. Indirect original state listener B 618 may be registered to model object B 604. Indirect original state listener C 620 may be registered to model object E 610.

When a first change to the hierarchical relationship tree is made to model object D 608, indirect original state listener B 618 and indirect original state listener A 616 registered to model object B 604 and model object A 602, respectively, may be notified. Indirect original state listener C 620 registered to model object E 610 is not considered by the notification mechanism because it is not part of the upward hierarchical relationship tree of model object D 608 where the change is made. If a second change to the hierarchical relationship tree is subsequently made to model object F 612, only indirect original state listener C 620 registered to model object E 610 may be notified. Since indirect original state listener B 618 and indirect original state listener A 616 already received notification of the previous change to the hierarchical relationship tree, indirect original state listener B 618 and indirect original state listener A 616 are not notified even though they are part of the upward hierarchical relationship tree of model object F 612 where the change is made. Then, if a third change to the hierarchical relationship tree is made to model object C 606, none of the registered indirect original state listeners 616-620 are notified. Since indirect original state listener A 616 registered to model object A 602 has received a notification of a previous change to the hierarchical relationship tree, indirect original state listener 616 is not notified. Indirect original state listener B 618 registered to model object B 604 and indirect original state listener C 620 registered to model object E 610 are not considered by the notification mechanism because neither listener is part of the upward hierarchical relationship tree of model object C 606 where the change is made. Thereafter, the first change to the hierarchical relationship tree made to model object D 608 may be reverted back to its original state. Since the effects of the second change and the third change are still present in the hierarchical relationship tree below each of the registered indirect original state listeners 616 and 618 none of the registered indirect original state listeners 616 and 618 are notified. Indirect original state listener C 620 registered to model object E 610 is not considered by the notification mechanism because it is not part of the upward hierarchical relationship tree of model object D 608 where the change is made. Then, if the second change to the hierarchical relationship tree made to model object F 612 is reverted back to its original state, a notification may sent to indirect original state listener C 620 and indirect original state listener B 618, since hierarchical relationship tree below model object B 604 has returned to an original state. Indirect original state listener A 616 registered to model object A 602 is not notified because the third change to model object C 606 is not yet reverted back to an original state. Finally, if the third change to the hierarchical relationship tree made to model object C 606 is reverted back to an original state, indirect original state listener A 616 may be notified since hierarchical relationship tree below model object A 602 has been reverted back to an original state.

Figure 7:
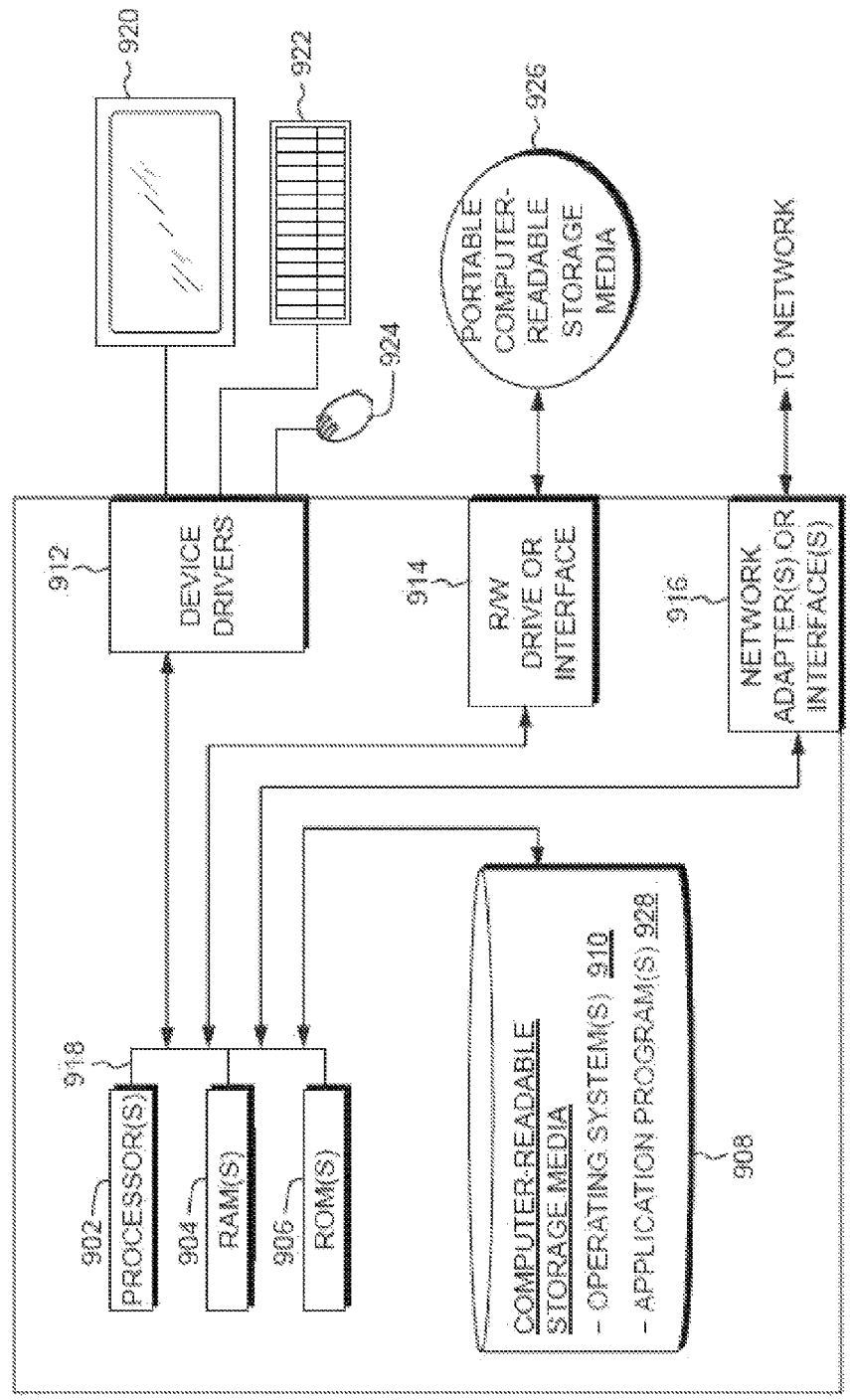
FIG. 7 is a functional block diagram of components of a client computing device and/or a server device of the listener notification system of FIG. 1, in accordance with an embodiment of the present invention.

FIG. 7 depicts a block diagram of components of a client computing device 110 and/or a server 120 of FIG. 1, in accordance with an embodiment of the present invention. It should be appreciated that FIG. 7 provides only an illustration of one implementation and does not imply any limitations with regard to the environments in which different embodiments may be implemented. Many modifications to the depicted environment may be made.

Client computing devices 110 and/or a server 120 may include one or more processors 902, one or more computer-readable RAMs 904, one or more computer-readable ROMs 906, one or more computer readable storage media 908, device drivers 912, read/write drive or interface 914, network adapter or interface 916, all interconnected over a communications fabric 918. Communications fabric 918 may be implemented with any architecture designed for passing data and/or control information between processors (such as microprocessors, communications and network processors, etc.), system memory, peripheral devices, and any other hardware components within a system.

One or more operating systems 910, and one or more application programs 928, for example, listener notification mechanism 112 and listener registration mechanism 128, are stored on one or more of the computer readable storage media 908 for execution by one or more of the processors 902 via one or more of the respective RAMs 904 (which typically include cache memory). In the illustrated embodiment, each of the computer readable storage media 908 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Client computing devices 110 and/or a server 120 may also include a R/W drive or interface 914 to read from and write to one or more portable computer readable storage media 926. Application programs 928 on client computing devices 110 and/or a server 120 may be stored on one or more of the portable computer readable storage media 926, read via the respective R/W drive or interface 914 and loaded into the respective computer readable storage media 908.

Client computing devices 110 and/or a server 120 may also include a network adapter or interface 916, such as a TCP/IP adapter card or wireless communication adapter (such as a 4G wireless communication adapter using OFDMA technology). Application programs 928 on computing devices 110 and/or a server 120 may be downloaded to the computing device from an external computer or external storage device via a network (for example, the Internet, a local area network or other wide area network or wireless network) and network adapter or interface 916. From the network adapter or interface 916, the programs may be loaded onto computer readable storage media 908. The network may comprise copper wires, optical fibers, wireless transmission, routers, firewalls, switches, gateway computers and/or edge servers.

Client computing devices 110 and/or a server 120 may also include a display screen 920, a keyboard or keypad 922, and a computer mouse or touchpad 924. Device drivers 912 interface to display screen 920 for imaging, to keyboard or keypad 922, to computer mouse or touchpad 924, and/or to display screen 920 for pressure sensing of alphanumeric character entry and user selections. The device drivers 912, R/W drive or interface 914 and network adapter or interface 916 may comprise hardware and software (stored on computer readable storage media 908 and/or ROM 906).

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Based on the foregoing, a computer system, method, and computer program product have been disclosed in accordance with the present invention. However, numerous modifications and substitutions can be made without deviating from the scope of the present invention. Therefore, the present invention has been disclosed by way of example and not limitation.

The foregoing description of various embodiments of the present invention has been presented for purposes of illustration and description. It is not intended to be exhaustive nor to limit the invention to the precise form disclosed. Many modifications and variations are possible. Such modification and variations that may be apparent to a person skilled in the art of the invention are intended to be included within the scope of the invention as defined by the accompanying claims.

What is claimed is:

1. A computer system for notifying a listener within a domain model that conserves resources, the computer system comprising:
   one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:
   registering a listener to one or more model objects based on a plurality of listener registration information, wherein the plurality of listener registration information includes one or more model objects to which the listener will register, a feature of the one or more model objects to which the listener will register, and a listener type of the listener, and wherein a list of each listener type is maintained, and wherein registering the listener comprises adding the listener to the list corresponding to the listener type, and wherein the listener receives at least one notification, and wherein the one or more model objects are part of a hierarchical relationship tree comprising a plurality of related model objects, and wherein the one or more model objects includes a first model object, a second model object, and a third model object, and wherein the first model object is referenced by the second model object, and wherein the first model object is referenced by the third model object, and wherein the listener is registered to the first model object, and wherein monitoring the hierarchical relationship tree for the observable event further comprises monitoring the second model object and the third model object for the observable event, and wherein determining that the first observable event to the hierarchical relationship tree has occurred further comprises determining that the first observable event has occurred to at least one of the second model object and the third model object, and wherein determining that the third observable event to the hierarchical relationship tree has occurred further comprises determining that the third observable event has occurred to at least one of the second model object and the third model object;
   determining that an initial change has occurred to the one or more model objects or one of the plurality of related model objects within the hierarchical relationship tree that alters the hierarchical relationship tree from an original state based on a notification algorithm, wherein the notification algorithm determines whether a change alters the hierarchical relationship tree from the original state or returns the hierarchical relationship tree to the original state;
   transmitting a first notification to the registered listener based on the determined initial change, wherein the transmitted notification includes a plurality of details corresponding to the determined initial change, and wherein the first notification may be transmitted to the registered listener based on the listener type associated with the registered listener;
   displaying a change indicator in a user interface beside the one or more model objects and each related model object within the plurality of related model objects affected by the determined initial change;
   determining that a subsequent change has occurred to the one or more model objects or one of the plurality of related model objects within the hierarchical relationship tree that returns the hierarchical relationship tree to the original state based on the notification algorithm;
   transmitting a second notification to the registered listener based on the determined subsequent change detailing the subsequent change has occurred; and
   removing the displayed change indicator in the user interface beside the one or more model objects and each related model object within the plurality of related model objects affected by the transmitted second notification.

* * * * *